United States Patent
Lee et al.

(10) Patent No.: US 11,697,673 B2
(45) Date of Patent: Jul. 11, 2023

(54) CAMP RECEPTOR PROTEIN VARIANT AND METHOD OF PRODUCING L-AMINO ACID USING THE SAME

(71) Applicant: CJ CHEILJEDANG CORPORATION, Seoul (KR)

(72) Inventors: Seok Myung Lee, Seoul (KR); Ki Yong Cheong, Seoul (KR); Chang Il Seo, Seoul (KR); Ji Sun Lee, Seoul (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 16/956,799

(22) PCT Filed: Jul. 25, 2019

(86) PCT No.: PCT/KR2019/009292
§ 371 (c)(1),
(2) Date: Jun. 22, 2020

(87) PCT Pub. No.: WO2020/111437
PCT Pub. Date: Jun. 4, 2020

(65) Prior Publication Data
US 2021/0363197 A1    Nov. 25, 2021

(30) Foreign Application Priority Data

Nov. 29, 2018    (KR) .................. 10-2018-0151043

(51) Int. Cl.
| | |
|---|---|
| C07K 14/245 | (2006.01) |
| C12N 15/70 | (2006.01) |
| C12P 13/08 | (2006.01) |
| C12P 13/22 | (2006.01) |
| C12N 1/20 | (2006.01) |
| C12R 1/19 | (2006.01) |

(52) U.S. Cl.
CPC ............ *C07K 14/245* (2013.01); *C12N 1/205* (2021.05); *C12P 13/08* (2013.01); *C12P 13/22* (2013.01); *C12R 2001/19* (2021.05)

(58) Field of Classification Search
None
See application file for complete search history.

(56) References Cited

U.S. PATENT DOCUMENTS

| | | |
|---|---|---|
| 8,242,242 B2 | 8/2012 | Kim et al. |
| 8,283,148 B2 | 10/2012 | Sorge et al. |
| 8,586,326 B2 | 11/2013 | El-Gewely |
| 10,035,826 B2 | 7/2018 | Masignani et al. |
| 10,125,178 B2 | 11/2018 | Wang et al. |
| 10,415,062 B2 | 9/2019 | Soucaille et al. |
| 2008/0286760 A1 | 11/2008 | Nikolaev et al. |
| 2014/0356389 A1 | 12/2014 | Masignani et al. |
| 2016/0362456 A1 | 12/2016 | Wang et al. |
| 2021/0363197 A1 | 11/2021 | Lee et al. |
| 2021/0388402 A1 | 12/2021 | Cheong et al. |

FOREIGN PATENT DOCUMENTS

| | | |
|---|---|---|
| CN | 103114069 A | 5/2013 |
| EP | 3 050 970 A1 | 8/2016 |
| JP | 10-84980 A | 4/1998 |
| JP | 2007-515160 A | 6/2007 |
| JP | 2010-506906 A | 3/2010 |
| KR | 10-1992-0008365 | 9/1992 |
| KR | 10-0058286 B1 | 1/1993 |
| KR | 10-0576342 | 4/2006 |
| KR | 10-2009-0076389 | 7/2009 |
| KR | 10-0966324 B1 | 6/2010 |
| KR | 10-2012-0083795 | 7/2012 |
| KR | 10-1261147 B1 | 4/2013 |
| KR | 10-2013-0082121 | 7/2013 |
| KR | 10-2014-0017213 | 2/2014 |
| KR | 10-1532129 B1 | 6/2015 |
| KR | 10-2016-0030053 A | 3/2016 |
| KR | 10-2016-0135025 | 11/2016 |
| KR | 10-2016-0135026 | 11/2016 |
| KR | 10-2017-0106674 | 9/2017 |
| KR | 10-1865998 B | 6/2018 |
| KR | 10-1991206 B1 | 6/2019 |
| KR | 10-1991207 B1 | 6/2019 |
| KR | 10-1996767 | 6/2019 |
| WO | 2008/050935 A1 | 5/2008 |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Yoo et al., J. Microbiol. Biotechnol. 10:670-676, 2000 (Year: 2000).*
Palego et al., J. Amino Acids 2016:8952520, 13 pages (Year: 2016).*
Desai et al., "Engineering transcription factors with novel DNA-binding specificity using comparative genomics," *Nucleic Acids Research* 37(8):2493-2503 (2009).
Khankal et al., "Transcriptional effects of CRP expression in *Escherichia coli*," *Journal of Biological Engineering* 3:13 (14 pages) (2009).
Lee et al., "Phenotypic engineering by reprogramming gene transcription using novel artificial transcription factors in *Escherichia coli*," *Nucleic Acids Research* 36(16):e102 (10 pages) (2008).
GenBank: AKC32461.1, "catabolite gene activator Crp [*Candidatus pantoea carbekii*]," 2 pages, Apr. 13, 2015.
NCBI Reference Sequence: WP_055103256.1, "cAMP-activated global transcriptional regulator CRP [*Pseudomonas endophytica*]," 2 pages, Oct. 23, 2015.

(Continued)

*Primary Examiner* — David Steadman
(74) *Attorney, Agent, or Firm* — Seed IP Law Group LLP

(57) ABSTRACT

The present disclosure relates to a variant of cAMP receptor protein of *Escherichia coli* with alanine at position 35, a microorganism including the same, and a method of producing an L-amino acid using the same.

10 Claims, No Drawings
Specification includes a Sequence Listing.

(56) References Cited

OTHER PUBLICATIONS

Bonarek et al., "cAMP Receptor Protein from *Escherichia coli* as a Model of Signal Transduction in Proteins—A Review," *J Mol Microbiol Biotechnol* 171-11 (2009).

Kohl et al. "The GlxR regulon of the amino acid producer *Corynebacterium glutamicum*: Detection of the corynebacterial core regulon and integration into the transcriptional regulatory network model," *Journal of Biotechnology* 143:239-246 (2009).

NCBI Reference Sequence: WP_000242747.1, cAMP-activated global transcriptional regulator CRP [*Escherichia coli*], 2 pages, Apr. 6, 2020.

NCBI Reference Sequence: WP_097301130.1, cAMP-activated global transcriptional regulator CRP [*Escherichia coli*], 2 pages, Apr. 6, 2020.

Sóberon-Chávez et al., "The transcriptional Regulators of the CRP Family Regulate Different Essential Bacterial Functions and Can Be Inherited Vertically and Horizontally," *Frontiers in Microbiology* 8(959), 8 pages, (May 2017).

Sondberg et al. "CRP Interacts Specifically With Sxy to Activate Transcription in *Escherichia coli*," *Frontiers in Microbiology* 10:2058, 8 pages (Aug. 2019).

UniParc—UPI000BE24849 cAMP-activated global transcriptional regulator CRP [*Escherichia coli*], Retrieved from the Internet: URL:https://www.uniprot.org/uniparc/UPI000BE24849, 2 pages, [retrieved on Dec. 13, 2021].

GenBank: PP187852.1, cAMP-activated global transcriptional regulator CRP [*Candidatus pantoea edessiphila*], 2 pages (Feb. 20, 2018).

UniProtKB—A0A2P5SZX3 (A0A2P5SZX3_9GAMM), 5 pages (May 23, 2018).

\* cited by examiner

CAMP RECEPTOR PROTEIN VARIANT AND METHOD OF PRODUCING L-AMINO ACID USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_468USPC_SEQUENCE_LISTING.txt. The text file is 7,307 bytes, was created on Jun. 15, 2020, and is being submitted electronically via EFS-Web.

TECHNICAL FIELD

The present disclosure relates to a cAMP receptor protein variant, a microorganism including the same, and a method of producing an L-amino acid using the same.

BACKGROUND ART

CRP (cyclic AMP receptor protein), also called CAP (catabolite activator protein), is the most well-known transcription regulator in *E. coli*. CRP is characterized by having a carbon source-dependent regulating mechanism, which is represented by 'catabolite repression'. This action is triggered by an intracellular concentration of cyclic AMP (hereinafter, referred to as 'cAMP'). In the presence of a preferred carbon source such as glucose, the activity of adenylate cyclase is inhibited to lower cAMP, and this signal inhibits the expression of catabolic genes. In the opposite case, the activity of adenylate cyclase is increased, and as a result, repressors are suppressed and expression of catabolic genes is initiated. In addition, CRP is known to play various roles such as intracellular signal transduction through cAMP, osmotic regulation, responses to urgent situations of cells, biofilm generation, nitrogen fixation, iron transport, etc.

Reportedly, 418 genes of *E. coli* are known to be regulated by CRP, but the corresponding mechanisms have not been yet clearly revealed (J Biol Eng. (2009) 24; 3:13). With such a wide range of regulatory abilities, CRP has the potential to show a variety of phenotypes by mutations. Because of its advantages, CRP has been studied as a target suitable for redesigning of strains at a cellular level, which are applicable to various environments. Recently, various experimentations have been conducted, such as a method of altering the expression of genes to be regulated by changing the degree of DNA binding by amino acid variation of CRP selected by bioinformatics (Nucleic Acids Research, (2009) 37: 2493-2503), a method of selecting *E. coli* resistant to heat, osmosis, and low temperature using an artificial transcription factor (ATF) prepared by fusion of a zinc finger DNA binding site and CRP ((Nucleic Acids Research, (2008) 36: e102), etc. In other words, since changes of the CRP expression promote a wide range of changes in expression of the downstream genes, CRP is likely to be a good tool for preparing microorganisms with useful traits.

DISCLOSURE

Technical Problem

The present inventors have developed a novel protein variant including one or more amino acid substitutions in an amino acid sequence of SEQ ID NO: 1, and they found that this protein variant may increase L-amino acid productivity, thereby completing the present disclosure.

Technical Solution

An object of the present disclosure is to provide a cAMP receptor protein variant.

Another object of the present disclosure is to provide a polynucleotide encoding the cAMP receptor protein variant.

Still another object of the present disclosure is to provide a vector including the polynucleotide.

Still another object of the present disclosure is to provide a microorganism of the genus *Escherichia* including the variant.

Still another object of the present disclosure is to provide a method of producing an L-amino acid, the method including culturing the microorganism of the genus *Escherichia* in a medium.

Still another object of the present disclosure is to provide use of the variant or the microorganism of the genus *Escherichia* including the variant in the production of L-amino acid.

Advantageous Effects

When a microorganism of the genus *Escherichia* producing an L-amino acid, the microorganism including a cAMP receptor protein variant of the present disclosure, is cultured, it is possible to produce the L-amino acid with a high yield. Accordingly, in industrial aspects, reduction of production costs, along with convenience of production, may be expected.

BEST MODE FOR CARRYING OUT THE INVENTION

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the above objects, one aspect of the present disclosure provides a cAMP receptor protein variant including one or more amino acid substitutions in an amino acid sequence of SEQ ID NO: 1. Specifically, the present disclosure provides the cAMP receptor protein variant including one or more amino acid substitutions in the amino acid sequence of SEQ ID NO: 1, wherein the amino acid substitutions include substitution of alanine for an amino acid at position 35 from the N-terminus. More specifically, the present disclosure provides the cAMP receptor protein variant including substitution of alanine for the amino acid at position 35 in the amino acid sequence of SEQ ID NO: 1.

As used herein, the term "cAMP receptor protein (CRP)" is the most well-known transcription regulator in *E. coli*, and CRP is also called 'dual regulator', because CRP itself has both functions of an activator and an inhibitor. CRP generally binds to a symmetric DNA sequence having 22 bases upstream of a structural gene to induce DNA bending, and CRP acts as the activator by allowing a first active site at the C-terminus and a second active site at the N-terminus to interact with RNA polymerase responsible for transcription, and it acts as the inhibitor by preoccupying the position to prevent the active protein from binding to the active site or by binding to the active protein to convert the structure into a structure that does not bind to the active site. The cAMP receptor protein is a cAMP receptor protein encoded by a crp gene.

The "cAMP receptor protein (cyclic AMP receptor protein, CRP)" of the present disclosure may be used interchangeably with a catabolite activator protein (CAP), a CRP protein, a CAP protein, etc.

In the present disclosure, a sequence of the CRP may be obtained from a known database GenBank at NCBI. For example, the CRP may be CRP derived from the genus Escherichia (Escherichia sp.), and more specifically, a polypeptide/protein including the amino acid sequence represented by SEQ ID NO: 1, but is not limited thereto. Further, a sequence having the same activity as the above amino acid sequence may be included without limitation. Further, the amino acid sequence of SEQ ID NO: 1 or an amino acid sequence having 80% or more homology or identity thereto may be included, but is not limited thereto. Specifically, the amino acid may include the amino acid of SEQ ID NO: 1 and an amino acid having at least 80%, 85%, 90%, 95%, 96%, 97%, 98%, or 99% or more homology or identity to SEQ ID NO: 1. Further, it is apparent that a protein having an amino acid sequence, part of which is deleted, modified, substituted, or added, may be within the scope of the present disclosure, as long as the amino acid sequence has the above homology or identity and exhibits efficacy corresponding to the above protein.

As used herein, the term "variant" refers to a polypeptide, one or more amino acids of which are different from the recited sequence in conservative substitutions and/or modifications, but it retains functions or properties of the protein. Variant polypeptides are different from an identified sequence by substitution, deletion, or addition of several amino acids. Such variants may be generally identified by modifying one of the above polypeptide sequences and evaluating the properties of the modified polypeptide. In other words, ability of a variant may be increased, unchanged, or decreased, as compared with that of a native protein. Such variants may be generally identified by modifying one of the above polypeptide sequences and evaluating reactivity of the modified polypeptide. Further, some variants may include those in which one or more portions, such as an N-terminal leader sequence or transmembrane domain, have been removed. Other variants may include variants in which a portion has been removed from the N- and/or C-terminus of a mature protein.

As used herein, the term "conservative substitution" means substitution of one amino acid with another amino acid that has similar structural and/or chemical properties. The variant may have, for example, one or more conservative substitutions while retaining one or more biological activities. Such amino acid substitutions may be generally made on the basis of similarity in polarity, charge, solubility, hydrophobicity, hydrophilicity, and/or the amphipathic nature of residues. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, proline, glycine, and tryptophan.

Further, variants may include deletion or addition of amino acids that have minimal influence on properties and a secondary structure of the polypeptide. For example, a polypeptide may be conjugated to a signal (or leader) sequence at the N-terminus of the protein, which co-translationally or post-translationally directs transfer of the protein. The polypeptide may also be conjugated to other sequence or a linker for identification, purification, or synthesis of the polypeptide.

As used herein, the term "cAMP receptor protein variant" is a cAMP receptor protein variant including one or more amino acid substitutions in an amino acid sequence of a polypeptide having cAMP receptor protein activity, wherein the amino acid substitutions include substitution of another amino acid for the amino acid at position 35 from the N-terminus. Specifically, the variant may include a protein variant, in which another amino acid is substituted for the amino acid at position 35 in the amino acid sequence of the polypeptide having AMP receptor protein activity. For example, the protein variant may include a protein variant in which variation occurs at position 35 from the N-terminus of the amino acid sequence of SEQ ID NO: 1. More specifically, the protein variant may be a protein in which another amino acid is substituted for the amino acid at position 35 of the amino acid sequence of SEQ ID NO: 1. The 'another amino acid' is not limited, as long as it is an amino acid other than L-glutamic acid which is the amino acid at position 35. Specifically, the variant may be a protein in which a hydrophobic amino acid is substituted for the amino acid at position 35 in the amino acid sequence of SEQ ID NO: 1. The hydrophobic amino acid may be one of L-alanine, L-glycine, L-valine, L-isoleucine, L-leucine, L-methionine, L-proline, L-phenylalanine, and L-tryptophan. More specifically, the variant may be a protein in which alanine is substituted for the amino acid at position 35 in the amino acid sequence of SEQ ID NO: 1, but is not limited thereto.

Further, the variant means a variant having a variation of the amino acid at position 35 from the N-terminus in the above-described amino acid sequence of SEQ ID NO: 1 and/or the amino acid sequence having at least 80%, 85%, 90%, 95%, 96%, 97%, 98%, or 99% or more homology or identity to SEQ ID NO: 1.

As used herein, the term "cAMP receptor protein variant" may be used interchangeably with a variant CRP protein, a CRP variant, a variant cAMP receptor protein, a variant CAP protein, a CAP variant, a variant catabolite activator protein, a catabolite activator protein variant, etc.

With respect to the objects of the present disclosure, a microorganism including the cAMP receptor protein variant is characterized by having high L-amino acid productivity, as compared with a microorganism including no cAMP receptor protein variant. The CRP variant is characterized by having a gene regulatory activity to increase the L-amino acid productivity, as compared with a native wild-type or non-variant cAMP receptor protein. This is meaningful in that the L-amino acid productivity may be increased by the microorganism introduced with the CRP variant of the present disclosure. Specifically, the L-amino acid may be L-threonine or L-tryptophan. However, any L-amino acid may be included without limitation, as long as it may be produced by introducing or including the variant cAMP receptor protein.

The cAMP receptor protein variant may be, for example, a variant including an amino acid sequence in which another amino acid is substituted for the amino acid at position 35 in the amino acid sequence represented by SEQ ID NO: 1, the variant composed of SEQ ID NO: 3. The variant in which alanine is substituted for the amino acid at position 35 in the amino acid sequence represented by SEQ ID NO: 1 may be composed of SEQ ID NO: 3, but is not limited thereto. Further, the CRP variant may include the amino acid sequence of SEQ ID NO: 3 or an amino acid sequence having 80% or more homology or identity thereto, but is not limited thereto. Specifically, the CRP variant of the present disclosure may include the protein having SEQ ID NO: 3 and a protein having at least 80%, 85%, 90%, 95%, 96%, 97%, 98%, or 99% or more homology or identity thereto. Further, it is apparent that a protein having an amino acid sequence, part of which is deleted, modified, substituted, or added, in addition to the amino acid sequence at position 35, may be within the scope of the present disclosure, as long as the amino acid sequence has the above homology or identity and exhibits efficacy corresponding to the above protein.

In other words, even though 'a protein having an amino acid sequence of a particular SEQ ID NO' is described herein, it is apparent that a protein having an amino acid sequence, part of which is deleted, modified, substituted, conservatively substituted, or added, may be used in the present disclosure, as long as it has activity identical or corresponding to that of the protein composed of the amino acid sequence of the corresponding SEQ ID NO. For example, as long as a protein has activity identical or corresponding to that of the variant protein, addition of a sequence that does not alter the function of the protein before and after the amino acid sequence, naturally occurring mutations, silent mutations or conservative substitutions thereof are not excluded. It is apparent that even though the protein has such a sequence addition or mutation, it falls within the scope of the present disclosure.

As used herein, the term 'homology' or 'identity' means the degree of relevance between two given amino acid sequences or nucleotide sequences, and may be expressed as a percentage.

The terms 'homology' and 'identity' may be often used interchangeably.

The sequence homology or identity of the conserved polynucleotide or polypeptide may be determined by standard alignment algorithms, and may be used with default gap penalties established by the used program. Substantially, homologous or identical sequences may hybridize under moderately or highly stringent conditions such that the full length of the sequence or at least about 50%, 60%, 70%, 80%, or 90% or more of the full-length may hybridize. Also, contemplated are polynucleotides that contain degenerate codons in place of codons in the hybridization.

Whether or not any two polynucleotide or polypeptide sequences have homology, similarity, or identity may be determined using known computer algorithms such as the "FASTA" program, using, for example, the default parameters as in Pearson et al (1988)[Proc. Natl. Acad. Sci. USA 85]: 2444, or determined using the Needleman-Wunsch algorithm (Needleman and Wunsch, 1970, J. Mol. Biol. 48: 443-453) as implemented in the Needleman program of the EMBOSS package (EMBOSS: The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, BLAST of the National Center for Biotechnology Information database, or ClustalW may be used to determine homology, similarity, or identity.

Homology, similarity, or identity of polynucleotides or polypeptides may be determined, for example, by comparing sequence information using a GAP computer program such as Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids), which are similar, divided by the total number of symbols in the shorter of the two sequences. Default parameters for the GAP program may include: (1) a unary comparison matrix (containing a value of 1 for identities and 0 for non-identities) and the weighted comparison matrix of Gribskov et al (1986) Nucl. Acids Res. 14: 6745, as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or gap open penalty of 10, gap extension penalty of 0.5); and (3) no penalty for end gaps. Therefore, as used herein, the term "homology" or "identity" represents relevance between sequences.

Another aspect of the present disclosure provides a polynucleotide encoding the CRP variant, or a vector including the polynucleotide.

As used herein, the term "polynucleotide" refers to a DNA or RAN strand having a predetermined length or more, which is a long chain polymer of nucleotides formed by linking nucleotide monomers via covalent bonds. More specifically, the polynucleotide refers to a polynucleotide fragment encoding the variant protein.

The polynucleotide encoding the CRP variant of the present disclosure may include any polynucleotide sequence without limitation, as long as it is a polynucleotide sequence encoding the cAMP receptor protein variant of the present disclosure. The polynucleotide encoding the CRP variant may include any sequence without limitation, as long as it is a sequence encoding the variant protein in which another amino acid is substituted for the amino acid at position 35 in the amino acid sequence of SEQ ID NO: 1. Specifically, the polynucleotide may be a polynucleotide sequence encoding the variant in which alanine is substituted for the amino acid at position 35 in the amino acid sequence of SEQ ID NO: 1. For example, the polynucleotide encoding the CRP variant of the present disclosure may be a polynucleotide sequence encoding the amino acid sequence of SEQ ID NO: 3, but is not limited thereto. More specifically, the polynucleotide may be composed of a polynucleotide sequence of SEQ ID NO: 4, but is not limited thereto. In the polynucleotide, various modifications may be made in the coding region provided that they do not change the amino acid sequence of the protein, due to codon degeneracy or in consideration of the codons preferred by the organism in which the protein is to be expressed. Therefore, it is apparent that, due to codon degeneracy, a polynucleotide which may be translated into the polypeptide composed of the amino acid sequence of SEQ ID NO: 3 or the polypeptide having homology or identity thereto may also be included.

Further, a probe which may be produced from a known nucleotide sequence, for example, a sequence which hybridizes with a complementary sequence to all or a part of the nucleotide sequence under stringent conditions to encode the CRP variant in which another amino acid is substituted for the amino acid at position 35 in the amino acid sequence of SEQ ID NO: 1 may also be included without limitation.

The term "stringent conditions" mean conditions under which specific hybridization between polynucleotides is allowed. Such conditions are described in detail in a literature (e.g., J. Sambrook et al., supra). For example, the stringent conditions may include, for example, conditions under which genes having high homology or identity, 80% or higher, 85% or higher, specifically 90% or higher, more specifically 95% or higher, much more specifically 97% or higher, particularly specifically 99% or higher homology or identity are hybridized with each other and genes having homology or identity lower than the above homology or identity are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS.

Although a mismatch between nucleotides may occur due to the stringency of hybridization, it is required that the two nucleic acids have a complementary sequence. The term "complementary" is used to describe the relationship between nucleotide bases which may hybridize with each other. For example, with respect to DNA, adenosine is complementary to thymine and cytosine is complementary to guanine.

Accordingly, the present disclosure may include not only the substantially similar nucleic acid sequences but also isolated nucleic acid fragments which are complementary to the entire sequence.

Specifically, the polynucleotide having homology or identity may be detected using hybridization conditions including the hybridization at a Tm value of 55° C. and the conditions described above. Additionally, the Tm value may be 60° C., 63° C., or 65° C., but is not limited thereto, and may be appropriately controlled by one of ordinary skill in the art according to the purposes.

Appropriate stringency for the hybridization of polynucleotides depends on the length and degree of complementarity of the polynucleotides, and the variables are well-known in the art (see Sambrook et al., supra, 9.50-9.51, 11.7-11.8).

As used herein, the term "vector" refers to a DNA construct that includes a nucleotide sequence of a polynucleotide encoding a target variant protein operably linked to an appropriate regulatory sequence to enable expression of the target variant protein in an appropriate host cell. The regulatory sequence may include a promoter capable of initiating transcription, any operator sequence for the regulation of such transcription, a sequence encoding an appropriate mRNA ribosome-binding domain, and a sequence regulating termination of transcription and translation. After the vector is transformed into the appropriate host cell, it may replicate or function independently of the host genome, and may be integrated into the genome itself.

The vector used in the present disclosure is not particularly limited, as long as it is able to replicate in the host cell, and any vector known in the art may be used. Examples of commonly used vectors may include a natural or recombinant plasmid, cosmid, virus, and bacteriophage. For instance, pWE15, M13, MBL3, MBL4, IXII, ASHII, APII, t10, t11, Charon4A, Charon21A, etc. may be used as a phage vector or cosmid vector. As a plasmid vector, pBR type, pUC type, pBluescriptll type, pGEM type, pTZ type, pCL type, and pET type, etc. may be used. Specifically, pDZ, pACYC177, pACYC184, pCL, pECCG117, pUC19, pBR322, pMW118, pCC1BAC vector, etc. may be used.

For example, a polynucleotide encoding a target variant protein in the chromosome may be replaced by a mutated polynucleotide using a vector for intracellular chromosomal insertion. The chromosomal insertion of the polynucleotide may be performed by any method known in the art, for example, homologous recombination, but is not limited thereto. A selection marker to confirm the chromosomal insertion may be further included. The selection marker is to select cells transformed with the vector, that is, to confirm insertion of the desired polynucleotide, and the selection marker may include markers providing selectable phenotypes, such as drug resistance, auxotrophy, resistance to cytotoxic agents, or expression of surface-modified proteins. Since only cells expressing the selection marker are able to survive or to show different phenotypes under the environment treated with a selective agent, the transformed cells may be selected. As still another aspect of the present disclosure, the present disclosure provides a microorganism producing the L-amino acid, the microorganism including the variant protein or the polynucleotide encoding the variant protein. Specifically, the microorganism including the variant protein and/or the polynucleotide encoding the variant protein may be a microorganism prepared by transforming with the vector including the polynucleotide encoding the variant protein, but is not limited thereto.

As used herein, the term "transformation" means the introduction of a vector including a polynucleotide encoding a target protein into a host cell in such a way that the protein encoded by the polynucleotide is expressed in the host cell. As long as the transformed polynucleotide may be expressed in the host cell, it may be integrated into and placed in the chromosome of the host cell, or it may exist extrachromosomally, or irrespective thereof. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette may include a promoter operably linked to the polynucleotide, transcriptional termination signals, ribosome binding sites, and translation termination signals. The expression cassette may be in the form of a self-replicable expression vector. Additionally, the polynucleotide as it is may be introduced into the host cell and operably linked to sequences required for expression in the host cell, but is not limited thereto.

As used herein, the term "operably linked" means a functional linkage between the polynucleotide sequence encoding the desired variant protein of the present disclosure and a promoter sequence which initiates and mediates transcription of the polynucleotide sequence.

Still another aspect of the present disclosure provides a microorganism of the genus Escherichia (Escherichia sp.) including the cAMP receptor protein variant.

As used herein, the term "microorganism including the CRP variant" may refer to a recombinant microorganism to express the CRP variant of the present disclosure. For example, the microorganism refers to a host cell or a microorganism which is able to express the variant by including the polynucleotide encoding the CRP variant or by transforming with the vector including the polynucleotide encoding the CRP variant. With respect to the objects of the present disclosure, the microorganism is a microorganism expressing the cAMP receptor protein variant including one or more amino acid substitutions in the amino acid sequence of SEQ ID NO: 1, and the microorganism may be a microorganism expressing the variant protein having the cAMP receptor protein activity, wherein the amino acid substitution is substitution of alanine for the amino acid at position 35 from the N-terminus, but is not limited thereto.

The microorganism including the CRP variant may be any microorganism, as long as it includes the CRP variant to express an L-amino acid, for example, L-threonine or L-tryptophan, but is not limited thereto. For example, the microorganism including the CRP variant may be a recombinant microorganism having increased L-amino acid productivity, which is prepared by expressing the CRP variant in a natural wild-type microorganism or in a microorganism producing the L-amino acid. The recombinant microorganism having increased L-amino acid productivity may be a microorganism having increased L-amino acid productivity, as compared with the natural wild-type microorganism or non-modified microorganism, wherein the L-amino acid may be L-threonine or L-tryptophan, but is not limited thereto.

As used herein, the term "microorganism producing the L-amino acid" includes a wild-type microorganism or a microorganism in which natural or artificial genetic modification occurs, and it may be a microorganism having a particular weakened or enhanced mechanism due to insertion of a foreign gene or due to enhancement or inactivation of activity of an endogenous gene, in which a genetic variation occurs or activity is enhanced to produce the desired L-amino acid. With respect to the objects of the present disclosure, the microorganism producing the L-amino acid may include the variant protein to have increased productivity of the desired L-amino acid. Specifically, the microorganism producing the L-amino acid or the microorganism having the L-amino acid productivity in the present disclosure may be a microorganism in which part of genes involved in the L-amino acid biosynthesis pathway is enhanced or weakened, or part of genes involved in the L-amino acid degradation pathway is enhanced or weakened.

The "non-modified microorganism" refers to a natural strain as it is, or a microorganism including no CRP variant, or a microorganism that is not transformed with the vector including the polynucleotide encoding the CRP variant. The "microorganism" may include any one of prokaryotic microorganisms and eukaryotic microorganisms, as long as it is able to produce the L-amino acid. For example, the microorganism may include microorganisms of the genus *Escherichia*, the genus *Erwinia*, the genus *Serratia*, the genus *Providencia*, the genus *Corynebacterium*, and the genus *Brevibacterium*. Specifically, the microorganism may be a microorganism of the genus *Escherichia*, and more specifically *E. coli*, but is not limited thereto.

Still another aspect of the present disclosure provides a method of producing the L-amino acid, the method including culturing a microorganism of the genus *Escherichia* in a medium, the microorganism producing the L-amino acid by including the cAMP receptor protein variant.

The terms 'cAMP receptor protein variant' and 'L-amino acid' are the same as described above.

In the method, the culturing of the microorganism may be, but is not particularly limited to, performed by known batch culture, continuous culture, fed-batch culture, etc. In this regard, the culture conditions are not particularly limited, but an optimal pH (e.g., pH 5 to 9, specifically pH 6 to 8, and most specifically pH 6.8) may be maintained by using a basic compound (e.g., sodium hydroxide, potassium hydroxide, or ammonia) or acidic compound (e.g., phosphoric acid or sulfuric acid). In addition, aerobic conditions may be maintained by introducing oxygen or oxygen-containing gas mixture to a cell culture. The culture temperature may be maintained at 20° C. to 45° C., and specifically at 25° C. to 40° C. The culture may be performed for about 10 hours to about 160 hours, but is not limited thereto. The L-amino acid produced by the above culture may be excreted to a culture medium or may remain inside the cells.

Furthermore, the culture medium to be used may include, as carbon sources, sugars and carbohydrates (e.g., glucose, sucrose, lactose, fructose, maltose, molasse, starch, and cellulose), oil and fat (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid) individually or in combination, but is not limited thereto. As nitrogen sources, nitrogen-containing organic compounds (e.g., peptone, yeast extract, meat broth, malt extract, corn steep liquor, soybean meal, and urea), or inorganic compounds (e.g., ammonium sulfate, ammonium chloride, ammonium phosphate, ammonium carbonate, and ammonium nitrate) may be used individually or in combination, but is not limited thereto. As phosphorus sources, dipotassium hydrogen phosphate, potassium dihydrogen phosphate, and corresponding sodium salts thereof may be used individually or in combination, but is not limited thereto. Further, the medium may include essential growth-stimulating substances including other metal salts (e.g., magnesium sulfate or iron sulfate), amino acids, and vitamins.

The method may further include collecting the L-amino acid from the microorganism or the medium.

A method of collecting the L-amino acid produced in the culturing of the present disclosure may collect the desired L-amino acid from the culture broth using an appropriate method known in the art according to the culture method. For example, centrifugation, filtration, anion exchange chromatography, crystallization, HPLC, etc., may be used, and the desired L-amino acid may be collected from the medium or microorganism using an appropriate method known in the art.

Further, the collecting may include a purification process, and may be performed using an appropriate method known in the art. Therefore, the L-amino acid to be collected may be a purified form or a fermentation broth of the microorganism including the L-amino acid (Introduction to Biotechnology and Genetic Engineering, A. J. Nair., 2008).

Still another aspect of the present disclosure provides use of the cAMP receptor protein variant in the production of L-amino acid, the cAMP receptor protein variant including one or more amino acid substitutions in the amino acid sequence of SEQ ID NO: 1.

Still another aspect of the present disclosure provides use of the microorganism of the genus *Escherichia* in the production of L-amino acid, the microorganism of the genus *Escherichia* including the cAMP receptor protein variant.

The term 'cAMP receptor protein variant' and 'L-amino acid' are the same as described above.

MODE FOR INVENTION

Hereinafter, the present disclosure will be described in more detail with reference to Examples. However, it is apparent to those skilled in the art that these Examples are for illustrative purposes only, and the scope of the present disclosure is not intended to be limited by these Examples.

Example 1. Preparation of Recombinant Vector pCC1BAC-Crp 1-1. Preparation of Crp Gene Fragment To obtain about 0.96 kb of a DNA fragment of SEQ ID NO: including crp gene and an expression regulatory region, genomic DNA (gDNA) of a wild-type *E. coli* W3110 was extracted using a Genomic-tip system of Qiagen (company), and PCR (polymerase chain reaction) was performed using the gDNA as a template and a PCR HL premix kit (manufactured by BIONEER Co., the same applies hereinafter). PCR for amplification of the crp gene fragment was performed using primers of SEQ ID NOS: 6 and 7 for 27 cycles consisting of denaturation at 95° C. for 30 sec, annealing at 56° C. for 30 sec, and elongation at 72° C. for 2 min.

The PCR product was digested with EcoR I, and electrophoresis on a 0.8% agarose gel and elution were performed to obtain a DNA fragment of 0.96 Kb (hereinafter, referred to as "crp fragment").

TABLE 1

| SEQ ID NO. | Name of primer | Sequence (5'-3') |
|---|---|---|
| 6 | crp-F | CACGAATTCTTTGCTACTCCACTGCGTCA |
| 7 | crp-R | ACACGAATTCTTAACGAGTGCCGTAAACG |

1-2. Preparation of Recombinant Vector pCC1BAC-Crp

Copycontrol pCC1BAC vector (EPICENTRE, USA) was treated with EcoR I, and electrophoresis on a 0.8% agarose gel and elution were performed to obtain a product, which was then ligated with the crp fragment obtained in Example 1-1, thereby preparing a pCC1BAC-crp plasmid.

Example 2. Preparation of Recombinant Vector pCC1BAC-Crp Variant Library 2-1. Preparation of Mutant Crp Fragment by Error-Prone PCR PCR was performed using the genomic DNA of a wild-type E. coli W3110 as a template and a diversify PCR random mutagenesis kit (catalog #: K1830-1, Table III, mutagenesis reactions 4) of clonetech. In detail, PCR was performed using the primers of SEQ ID NOS: 6 and 7 as used in Example 1-1 for 27 cycles consisting of denaturation at 94° C. for 30 sec and elongation at 68° C. for 1 min.

The PCR product was digested with EcoR I, and electrophoresis on a 0.8% agarose gel and elution were performed to obtain a mutated crp fragment of 0.96 Kb (hereinafter, referred to as "crp$^m$ fragment").

2-2. Preparation of Recombinant Vector pCC1BAC-Crp Variant Library

A vector pCC1BAC was treated with a restriction enzyme EcoR I, and then treated with alkaline phosphatase (NEB). The prepared vector was ligated with the crp$^m$ fragment obtained in Example 2-1, and the ligation product was transformed into TransforMax EPI300 Electrocompetent E. coli (EPICENTRE, USA) by electrophoresis. The transformed strain was cultured on an LB solid medium (15 ug/ml) containing chloramphenicol to select colonies. The colonies thus obtained were collected and subjected to plasmid prep, thereby preparing a pCC1BAC-crp$^m$ library.

Example 3. Introduction of Crp Variant Library into Threonine-Producing Stain and Selection of Growth-Improved Strain 3-1. Introduction of pCC1BAC-crp$^m$ Library into Threonine-Producing Stain The pCC1BAC-crp$^m$ library obtained in Example 2 was transformed into electro-competent cells of KCCM10541 which is a threonine-producing microorganism by electroporation. E. coli KCCM10541 (Korean Patent No. 10-0576342) used in this Example is E. coli prepared by inactivating galR gene in an L-threonine-producing E. coli KFCC10718 (Korean Patent No. 10-0058286).

As a control group of the pCC1BAC-crp$^m$ library-introduced microorganism, pCC1BAC-crp was transformed into KCCM10541 in the same manner as above to prepare KCCM10541/pCC1BAC-crp(WT).

3-2. Comparison of Growth Rate of Recombinant Microorganism

An M9 minimal medium containing 1% glucose and 0.2 g/L of yeast extract was dispensed in a deep well microplate, and then the transformant and the control strain prepared in Example 3-1 were seeded thereto, respectively. The strains were cultured using a micro size constant temperature incubator shaker (TAITEC, Japan) under conditions of 37° C. and 200 rpm by an HTS (High Throughput Screening) method for 20 hours, and growth-improved strains were selected. Among them, one kind of strain was finally selected (Table 2).

KCCM10541 strain introduced with the wild-type crp gene showed a slight increase in the OD value due to additional introduction of crp, whereas the growth-improved transformant showed a high OD value after the same culture time, as compared with the wild-type crp-introduced strain. Further, the selected crp variant was subjected to plasmid mini-prep, followed by sequencing analysis. The results are summarized in Table 2.

TABLE 2

Information of growth-improved transformant after introduction of crp$^m$ library into threonine-producing strain

| Strain | OD600 | Variation |
|---|---|---|
| KCCM10541/pCC1BAC | 2.3 | — |
| KCCM10541/pCC1BAC-crp(WT) | 2.8 | — |
| KCCM10541/pCC1BAC-crpTM4 | 3.5 | E35A |

3-3. Comparison of Threonine Titer of Recombinant Microorganism

To measure the threonine titer of the recombinant microorganism selected in Example 3-2, the recombinant microorganism was cultured in a threonine titration medium prepared as in the composition of the following Table 3 to examine improvement of L-threonine productivity.

TABLE 3

Composition of threonine titration medium

| Composition | Concentration (per liter) |
|---|---|
| Glucose | 70 g |
| KH$_2$PO$_4$ | 2 g |
| (NH$_4$)$_2$SO$_4$ | 25 g |
| MgSO$_4$•7H$_2$O | 1 g |
| FeSO$_4$•7H$_2$O | 5 mg |
| MnSO$_4$•4H$_2$O | 5 mg |
| Yeast extract | 2 g |
| Calcium carbonate | 30 g |
| pH | 6.8 |

In detail, each one platinum loop of E. coli KCCM10541/pCC1BAC-crp(WT) and E. coli KCCM10541/pCC1BACcrpTM4 cultured overnight on an LB solid medium in an incubator at 33° C. was inoculated in 25 mL of the titration medium of Table 3, respectively, and then cultured in an incubator at 33° C. and 200 rpm for 48 hours to compare sugar consumption rates and threonine concentrations.

As a result, as described in the following Table 4, the KCCM10541/pCC1BAC-crp(WT) strain as the control group showed sugar consumption of 26.1 g/L at 24 hours, whereas the mutant crpTM4-introduced strain showed about 16% and 11% improvement in the sugar consumption rate, as compared with the mother strain and the wild-type crp-introduced strain, respectively.

Further, when cultured for 48 hours, the wild-type crp-introduced strain showed 29.0 g/L of L-threonine production, whereas L-threonine production of the mutant strain obtained above was increased up to 31.0 g/L even though the culture speed was increased, showing about 8% and 7% improvement in the concertation, as compared with the mother strain and the wild-type crp-introduced strain, respectively.

Since the introduction of crp variant increased the yield and the sugar consumption of the strain, it seems to be a good variant trait, which may greatly contribute to improvement of production efficiency during fermentation.

TABLE 4

Comparison of titer of threonine strain including crp variant

| Strain | Sugar consumption (g/L)* | Threonine (g/L)** |
|---|---|---|
| KCCM10541/pCC1BAC | 25.0 | 28.8 |
| KCCM10541/pCC1BAC-crp(WT) | 26.1 | 29.0 |
| KCCM10541/pCC1BAC-crpTM4 | 29.0 | 31.0 |

*24-hr measured value
**48-hr measured value

Example 4. Introduction of pCC1BAC-crpTM4 Variant into Tryptophan-Producing Strain 4-1. Introduction of pCC1BAC-crpTM4 into Screening Strain pCC1BAC-crpTM4 obtained in Example 3 was transformed into electro-competent cells of a tryptophan-producing strain KCCM11166P by electroporation. KCCM11166P used in this Example is an L-tryptophan-producing *E. coli* in which tehB gene was deleted and NAD kinase activity was enhanced (Korean Patent No. 10-1261147).

As a control group of the pCC1BAC-crpTM4-introduced microorganism, pCC1BAC-crp(WT) was transformed into KCCM11166P in the same manner as above to prepare KCCM11166P/pCC1BAC-crp(WT).

4-2. Comparison of Growth Rate of Recombinant Microorganism

An M9 minimal medium containing 1% glucose and 0.2 g/L of yeast extract was dispensed in a deep well microplate, and then the transformant and the control strain prepared as in Example 4-1 were seeded thereto, respectively. The strains were cultured using a micro size constant temperature incubator shaker (TAITEC, Japan) under conditions of 37° C. and 200 rpm by an HTS (High Throughput Screening) method for 16 hours to confirm growth improvement of KCCM11166P/pCC1BAC-crpTM4 transformant (Table 5).

KCCM11166P strain introduced with the wild-type crp gene showed an equivalent level of OD due to additional introduction of crp after the same culture time, whereas the growth-improved transformant showed a high OD value, as compared with the wild-type crp.

TABLE 5

Information of growth-improved transformant after introduction of crpTM4 into tryptophan-producing strain

| Strain | OD600 | Variation |
|---|---|---|
| KCCM11166P/pCC1BAC | 3.4 | — |
| KCCM11166P/pCC1BAC-crp(WT) | 3.5 | — |
| KCCM11166P/pCC1BAC-crpTM4 | 4.0 | E35A |

4-3. Comparison of Tryptophan Titer of Recombinant Microorganism

To measure the tryptophan titer of the recombinant microorganism prepared in Example 4-2, the recombinant microorganism was cultured in a tryptophan titration medium prepared as in the composition of the following Table 6 to examine improvement of L-tryptophan productivity.

TABLE 6

Composition of tryptophan titration medium

| Composition | Concentration (per liter) |
|---|---|
| Glucose | 60 g |
| $K_2HPO_4$ | 1 g |
| $(NH_4)_2SO_4$ | 10 g |
| NaCl | 1 g |
| $MgSO_4 \cdot 7H_2O$ | 1 g |
| Sodium citrate | 5 g |
| Yeast extract | 2 g |
| Calcium carbonate | 40 g |
| Sodium citrate | 5 g |
| Phenyl alanine | 0.15 g |
| Tyrosine | 0.1 g |
| pH | 6.8 |

In detail, each one platinum loop of *E. coli* KCCM11166P/pCC1BAC-crp(WT) and *E. coli* KCCM11166P/pCC1BAC-crpTM4 cultured overnight on an LB solid medium in an incubator at 37° C. was inoculated in 25 mL of the titration medium of Table 6, respectively, and then cultured in an incubator at 37° C. and 200 rpm for 48 hours to compare sugar consumption rates and tryptophan concentrations.

As a result, as described in the following Table 7, the KCCM11166P/pCC1BAC-crp(WT) strain as the control group showed sugar consumption of 30.2 g/L at 22 hours, whereas the mutant crpTM4-introduced strain showed about 146% and 9% improvement in the sugar consumption rate, as compared with the mother strain and the wild-type crp-introduced strain, respectively.

When cultured for 48 hours, the wild-type crp-introduced strain showed 8.4 g/L of L-tryptophan production, whereas L-tryptophan production of the mutant strain obtained above was increased up to 9.7 g/L even though the culture speed was increased, showing about 18% and 15% improvement in the concertation, as compared with the mother strain and the wild-type crp-introduced strain, respectively.

Since the introduction of crp variant increased the sugar consumption of the strain and the yield, it seems to be a good variant trait, which may greatly contribute to improvement of production efficiency during fermentation.

TABLE 7

Comparison of titer of tryptophan strain including crp variant

| Strain | Sugar consumption (g/L)* | Tryptophan (g/L)** |
|---|---|---|
| KCCM11166P/pCC1BAC | 29.0 | 8.2 |
| KCCM11166P/pCC1BAC-crp(WT) | 30.2 | 8.4 |
| KCCM11166P/pCC1BAC-crpTM4 | 33.0 | 9.7 |

*22-hr measured value
**48-hr measured value

Example 5. Introduction of Effective Crp Variant Endogenous Vector into Wild-Type *E. coli*

5-1. Introduction of Effective pCC1BAC-Crp Variant into Wild-Type-Derived Threonine-Producing Strain To examine whether the vector including the crp variant screened in Example 3 also showed equivalent effects in the wild-type strain, the pCC1BAC-crp(WT) or pCC1BAC-crpTM4 vector was transformed into the wild-type derived strain capable of producing threonine by electroporation, respectively. Further, a pCC1BAC-crp(WT)-introduced strain was prepared as a control group.

The wild-type derived strain capable of producing threonine used in this Example is W3110::PcysK-ppc/pACYC184-thrABC. W3110::PcysK-ppc/pACYC184-thrABC is a strain in which a native promoter of a ppc gene encoding phosphoenolpyruvate carboxylase on the chromosome was substituted with a promoter of a cysK gene, and a threonine biosynthesis operon gene was introduced in the form of a vector to increase the number of copy, thereby increasing threonine productivity. In detail, a W3110::PcycK-ppc strain was prepared using pUCpcycKmloxP in the same manner as described in Korean Patent No. 10-0966324, and pACYC184-thrABC (Korean Patent No. 10-1865998) was transformed into the strain by electroporation.

The prepared strains were cultured in a threonine test medium prepared as in the composition of the following Table 8, and growth rates and L-threonine productivities thereof were compared.

TABLE 8

Composition of threonine test medium

| Composition | Concentration (per liter) |
|---|---|
| Glucose | 70 g |
| KH$_2$PO$_4$ | 2 g |
| (NH$_4$)$_2$SO$_4$ | 25 g |
| MgSO$_4$•7H$_2$O | 1 g |
| FeSO$_4$•7H$_2$O | 5 mg |
| MnSO$_4$•7H$_2$O | 5 mg |
| DL-methionine | 0.15 g |
| Yeast extract | 2 g |
| Calcium carbonate | 30 g |
| pH | 6.8 |

In detail, each one platinum loop of W3110 and respective strains cultured overnight on an LB solid medium in an incubator at 33° C. was inoculated in 25 mL of the titration medium of Table 8, respectively, and then cultured in an incubator at 33° C. and 200 rpm for 48 hours. The results thereof are shown in the following Table 9. As shown in the following results, the variant protein selected in the present disclosure is also able to efficiently produce threonine with a high yield in the wild-type strain.

TABLE 9

Results of testing growth and threonine productivity of wild-type-derived strain

| Strain | OD | Threonine (g/L)** |
|---|---|---|
| W3110::PcysK-ppc/pACYC184-thrABC/pCC1BAC | 10.8 | 1.5 |
| W3110::PcysK-ppc/pACYC184-thrABC/pCC1BAC-crp(WT) | 11.0 | 1.6 |
| W3110::PcysK-ppc/pACYC184-thrABC/pCC1BAC-crpTM4 | 13.0 | 2.2 |

5-2. Introduction of Effective pCC1BAC-Crp Variant into Wild-Type-Derived Tryptophan-Producing Strain To examine whether the vector including the crp variant screened in Example 4 also showed equivalent effects in the wild-type strain, the pCC1BAC-crp(WT) or pCC1BAC-crpTM4 vector was transformed into the wild-type derived strain capable of producing tryptophan, respectively.

The wild-type derived strain capable of producing tryptophan used in this Example is W3110 trpΔ2/pCL-Dtrp_att-trpEDCBA. W3110 trpΔ2/pCL-Dtrp_att-trpEDCBA is a strain introduced with a vector in which a regulatory mechanism of a tryptophan operon regulatory region was released and tryptophan operon expression was enhanced to overexpress tryptophan (Korean Patent No. 10-1532129). The vector-introduced strains were cultured in a tryptophan test medium prepared as in the composition of the following Table 10, and L-tryptophan productivities thereof were compared.

TABLE 10

Composition of tryptophan test medium

| Composition | Concentration (per liter) |
|---|---|
| Glucose | 2 g |
| K$_2$HPO$_4$ | 1 g |
| (NH$_4$)$_2$SO$_4$ | 12 g |
| NaCl | 1 g |
| Na$_2$HPO$_4$•H$_2$O | 5 g |
| MgSO$_4$•H$_2$O | 1 g |
| MnSO$_4$•H$_2$O | 15 mg |
| CuSO$_4$•H$_2$O | 3 mg |
| ZnSO$_4$•H$_2$O | 30 mg |
| Sodium citrate | 1 g |
| Yeast extract | 1 g |
| Phenyl alanine | 0.15 g |
| pH | 6.8 |

In detail, each one platinum loop of the strains cultured overnight on an LB solid medium in an incubator at 37° C. was inoculated in 25 mL of the test medium of Table 9, respectively, and then cultured in an incubator at 37° C. and 200 rpm for 48 hours. OD values and tryptophan concentrations were compared and shown in Table 11. As shown in the following results, the variant protein selected in the present disclosure is also able to efficiently produce tryptophan with a high yield in the wild-type strain.

TABLE 11

Results of testing growth and tryptophan productivity of wild-type-derived strain

| Strain | OD | Tryptophan (g/L)** |
|---|---|---|
| W3110 trpΔ2/pCL-Dtrp_att-trpEDCBA/pCC1BAC | 10.8 | 0.5 |
| W3110 trpΔ2/pCL-Dtrp_att-trpEDCBA/pCC1BAC-crp(WT) | 11.0 | 0.6 |
| W3110 trpΔ2/pCL-Dtrp_att-trpEDCBA/pCC1BAC-crpTM4 | 13.0 | 1.0 |

The present inventors designated the KCCM11166P-based, pCC1BAC-crpTM4-introduced strain having improved tryptophan productivity and sugar consumption rate (KCCM11166P/pCC1BAC-crpTM4) as "CA04-2809", and then deposited the strain to the Korean Culture Center of Microorganisms (KCCM) which is the international depository authority under the Budapest Treaty, on Nov. 7, 2018 with the Accession No. KCCM12375P.

These results indicate that the sugar consumption rate was improved and the L-amino acid productivity was increased in the crp variant-introduced microorganism of the genus *Escherichia* of the present disclosure, and consequently, the L-amino acid productivity was increased, as compared with the non-modified strain.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A cAMP receptor protein variant, wherein the cAMP receptor protein variant has transcription regulator activity of a cAMP receptor protein, has at least 80% sequence identity to the sequence of SEQ ID NO: 1, and has alanine at the position corresponding to position 35 of SEQ ID NO: 1.

2. A polynucleotide encoding a cAMP receptor protein variant, wherein the cAMP receptor protein variant has transcription regulator activity of a cAMP receptor protein, has at least 80% sequence identity to the sequence of SEQ ID NO: 1, and has alanine at the position corresponding to position 35 of SEQ ID NO: 1.

3. A vector comprising the polynucleotide of claim 2.

4. A microorganism of the genus *Escherichia* comprising a cAMP receptor protein variant, wherein the cAMP receptor protein variant has transcription regulator activity of a cAMP receptor protein, has at least 80% sequence identity to the sequence of SEQ ID NO: 1, and has alanine at the position corresponding to position 35 of SEQ ID NO: 1.

5. The microorganism of the genus *Escherichia* of claim 4, wherein the microorganism of the genus *Escherichia* is *E. coli*.

6. The microorganism of the genus *Escherichia* of claim 4, wherein the microorganism of the genus *Escherichia* produces an L-amino acid.

7. The microorganism of the genus *Escherichia* of claim 6, wherein the L-amino acid is L-threonine or L-tryptophan.

8. A method of producing an L-amino acid, the method comprising:
culturing a microorganism of the genus *Escherichia* in a medium to produce the L-amino acid, wherein the microorganism comprises a cAMP receptor protein variant, wherein the cAMP receptor protein variant has transcription regulator activity of a cAMP receptor protein, has at least 80% sequence identity to the sequence of SEQ ID NO: 1, and has alanine at the position corresponding to position 35 of SEQ ID NO: 1.

9. The method of claim 8, further comprising collecting the L-amino acid from the microorganism or the medium.

10. The method of claim 8, wherein the L-amino acid is L-threonine or L-tryptophan.

* * * * *

UNITED STATES PATENT AND TRADEMARK OFFICE
CERTIFICATE OF CORRECTION

PATENT NO. : 11,697,673 B2
APPLICATION NO. : 16/956799
DATED : July 11, 2023
INVENTOR(S) : Seok Myung Lee et al.

It is certified that error appears in the above-identified patent and that said Letters Patent is hereby corrected as shown below:

On the Title Page

<u>Item (54) and in the Specification Column 1 Lines 1-3:</u>
"CAMP RECEPTOR PROTEIN VARIANT AND METHOD OF PRODUCING L-AMINO ACID USING THE SAME"

Should read:
--cAMP RECEPTOR PROTEIN VARIANT AND METHOD OF PRODUCING L-AMINO ACID USING THE SAME--

Signed and Sealed this
Eighth Day of August, 2023

Katherine Kelly Vidal
*Director of the United States Patent and Trademark Office*

```
SEQUENCE LISTING

<160> NUMBER OF SEQ ID NOS: 7

<210> SEQ ID NO 1
<211> LENGTH: 210
<212> TYPE: PRT
<213> ORGANISM: Unknown
<220> FEATURE:
<223> OTHER INFORMATION: CRP

<400> SEQUENCE: 1

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Lys Leu Ile His
                20                  25                  30

Gln Gly Glu Lys Ala Glu Thr Leu Tyr Tyr Ile Val Lys Gly Ser Val
            35                  40                  45

Ala Val Leu Ile Lys Asp Glu Glu Gly Lys Glu Met Ile Leu Ser Tyr
    50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
    115                 120                 125

Ser Glu Lys Val Gly Asn Leu Ala Phe Leu Asp Val Thr Gly Arg Ile
130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
    195                 200                 205

Thr Arg
    210
```

<210> SEQ ID NO 2
<211> LENGTH: 633
<212> TYPE: DNA
<213> ORGANISM: Unknown
<220> FEATURE:
<223> OTHER INFORMATION: CRP

<400> SEQUENCE: 2

```
atggtgcttg gcaaaccgca aacagacccg actctcgaat ggttcttgtc tcattgccac    60
attcataagt acccatccaa gagcaagctt attcaccagg gtgaaaaagc ggaaacgctg   120
tactacatcg ttaaaggctc tgtggcagtg ctgatcaaag acgaagaggg taaagaaatg   180
atcctctcct atctgaatca gggtgatttt attggcgaac tgggcctgtt tgaagagggc   240
caggaacgta gcgcatgggt acgtgcgaaa accgcctgtg aagtggctga aatttcgtac   300
aaaaaatttc gccaattgat tcaggtaaac ccggacattc tgatgcgttt gtctgcacag   360
atggcgcgtc gtctgcaagt cacttcagag aaagtgggca acctggcgtt cctcgacgtg   420
acgggccgca ttgcacagac tctgctgaat ctggcaaaaa accagacgc tatgactcac   480
ccggacggta tgcaaatcaa aattacccgt caggaaattg gtcagattgt cggctgttct   540
cgtgaaaccg tgggacgcat tctgaagatg ctggaagatc agaacctgat ctccgcacac   600
ggtaaaaacca tcgtcgttta cggcactcgt taa                                633
```

<210> SEQ ID NO 3
<211> LENGTH: 210
<212> TYPE: PRT
<213> ORGANISM: Unknown
<220> FEATURE:
<223> OTHER INFORMATION: modified CRP

<400> SEQUENCE: 3

```
Met Val Leu Gly Lys Pro Gln Thr Asp Pro Thr Leu Glu Trp Phe Leu
1               5                   10                  15

Ser His Cys His Ile His Lys Tyr Pro Ser Lys Ser Lys Leu Ile His
            20                  25                  30

Gln Gly Ala Lys Ala Glu Thr Leu Tyr Tyr Ile Val Lys Gly Ser Val
        35                  40                  45

Ala Val Leu Ile Lys Asp Glu Glu Gly Lys Glu Met Ile Leu Ser Tyr
    50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
        115                 120                 125

Ser Glu Lys Val Gly Asn Leu Ala Phe Leu Asp Val Thr Gly Arg Ile
    130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
```

```
            195                 200                 205

Thr Arg
    210

<210> SEQ ID NO 4
<211> LENGTH: 633
<212> TYPE: DNA
<213> ORGANISM: Unknown
<220> FEATURE:
<223> OTHER INFORMATION: modified CRP

<400> SEQUENCE: 4
atggtgcttg gcaaaccgca aacagacccg actctcgaat ggttcttgtc tcattgccac      60
attcataagt acccatccaa gagcaagctt attcaccagg gtgcaaaagc ggaaacgctg     120
tactacatcg ttaaaggctc tgtggcagtg ctgatcaaag acgaagaggg taaagaaatg     180
atcctctcct atctgaatca gggtgatttt attggcgaac tgggcctgtt tgaagagggc     240
caggaacgta gcgcatgggt acgtgcgaaa accgcctgtg aagtggctga atttcgtac      300 aaaaaatttc gccaattgat tcaggtaaac ccggacattc tgatgcgttt gtctgcacag     360
atggcgcgtc gtctgcaagt cacttcagag aaagtgggca acctggcgtt cctcgacgtg     420
acgggccgca ttgcacagac tctgctgaat ctggcaaaac aaccagacgc tatgactcac     480
ccggacggta tgcaaatcaa aattacccgt caggaaattg gtcagattgt cggctgttct     540
cgtgaaaccg tgggacgcat tctgaagatg ctggaagatc agaacctgat ctccgcacac     600
ggtaaaacca tcgtcgttta cggcactcgt taa                                 633

<210> SEQ ID NO 5
<211> LENGTH: 933
<212> TYPE: DNA
<213> ORGANISM: Unknown
<220> FEATURE:
<223> OTHER INFORMATION: crp and expression control region

<400> SEQUENCE: 5
tttgctactc cactgcgtca attttcctga cagagtacgc gtactaacca aatcgcgcaa      60
cggaaggcga cctgggtcat gctgaagcga gacaccagga gacacaaagc gaaagctatg     120
ctaaaacagt caggatgcta cagtaataca ttgatgtact gcatgtatgc aaaggacgtc     180
acattaccgt gcagtacagt tgatagcccc ttcccaggta gcgggaagca tatttcggca     240
atccagagac agcggcgtta tctggctctg agaaagctt ataacagagg ataaccgcgc     300
atggtgcttg gcaaaccgca aacagacccg actctcgaat ggttcttgtc tcattgccac     360
attcataagt acccatccaa gagcaagctt attcaccagg gtgaaaaagc ggaaacgctg     420
tactacatcg ttaaaggctc tgtggcagtg ctgatcaaag acgaagaggg taaagaaatg     480
atcctctcct atctgaatca gggtgatttt attggcgaac tgggcctgtt tgaagagggc     540
caggaacgta gcgcatgggt acgtgcgaaa accgcctgtg aagtggctga atttcgtac      600 aaaaaatttc gccaattgat tcaggtaaac ccggacattc tgatgcgttt gtctgcacag     660
atggcgcgtc gtctgcaagt cacttcagag aaagtgggca acctggcgtt cctcgacgtg     720
acgggccgca ttgcacagac tctgctgaat ctggcaaaac aaccagacgc tatgactcac     780
ccggacggta tgcaaatcaa aattacccgt caggaaattg gtcagattgt cggctgttct     840
cgtgaaaccg tgggacgcat tctgaagatg ctggaagatc agaacctgat ctccgcacac     900
ggtaaaacca tcgtcgttta cggcactcgt taa                                 933
```

```
<210> SEQ ID NO 6
<211> LENGTH: 29
<212> TYPE: DNA
<213> ORGANISM: Artificial Sequence
<220> FEATURE:
<223> OTHER INFORMATION: crp-F primer

<400> SEQUENCE: 6
cacgaattct ttgctactcc actgcgtca                                        29

<210> SEQ ID NO 7
<211> LENGTH: 29
<212> TYPE: DNA
<213> ORGANISM: Artificial Sequence
<220> FEATURE:
<223> OTHER INFORMATION: crp-R primer

<400> SEQUENCE: 7
acacgaattc ttaacgagtg ccgtaaacg                                        29
```